United States Patent [19]

Schaefer

[11] Patent Number: 4,598,701
[45] Date of Patent: Jul. 8, 1986

[54] SHOULDER ABDUCTION SPLINT

[75] Inventor: Daniel J. Schaefer, Greenville, S.C.

[73] Assignee: Span-America Medical Systems, Inc., Greenville, S.C.

[21] Appl. No.: 609,457

[22] Filed: May 11, 1984

[51] Int. Cl.$^4$ ............................................. A61F 5/04
[52] U.S. Cl. .................................................. 128/87 C
[58] Field of Search ................ 128/87 C, 77, 87 R, 128/94, 133, 83, 68, 165, 88, 80 A

[56] References Cited

U.S. PATENT DOCUMENTS

| | | | |
|---|---|---|---|
| 3,284,817 | 11/1966 | Landwirth | 128/80 R X |
| 4,241,731 | 12/1980 | Pauley | 128/94 |
| 4,270,235 | 6/1981 | Gutmann | 128/68 X |
| 4,392,489 | 7/1983 | Wagner, Sr. | 128/80 A |

FOREIGN PATENT DOCUMENTS 2744518 4/1978 Fed. Rep. of Germany .... 128/87 R

OTHER PUBLICATIONS

Flyer entitled "Application Instructions for Shoulder Abduction Support" (one pg.) by Orthopedic Equipment Co., Bourbon, Indiana, Form No. 606, Oct. 1977.

*Primary Examiner*—Mickey Yu
*Attorney, Agent, or Firm*—Dority & Manning

[57] ABSTRACT

A shoulder abduction splint constructed from a unitary block of synthetic foam material is illustrated providing in a single disposable support a splint for selectively positioning the arm in a substantially 90 degree position with respect to the body or an intermediate position with respect to the body as dictated by the results of surgery on the shoulder.

6 Claims, 6 Drawing Figures

SHOULDER ABDUCTION SPLINT

BACKGROUND OF THE INVENTION

Abduction supports for the shoulder are commonly provided in the form of a bolster which is covered with cloth and provided with cloth straps in order to provide a support at an approximately 45 degree angle between the arm and the body. Such supports have disadvantages in that localized deformation with air circulation for the comfort and convenience of the patient may not be readily accomplished with the prior cloth coverings which tend to produce a hammock effect. It is difficult to immobilize the limbs because of sliding on the cloth cover. Alternatively, should it be desirable to position the arm in a substantially 90 degree position what is known as an airplane support is commonly used. These supports include a concave plate with openings therein which is positioned against the body with a similar metal concave support extending outwardly at right angles. A common shoulder operation is known as a rotator cuff repair and with such operations, it is difficult to predict in advance the desirable angular position for the arm.

Accordingly, it is an important object of this invention to provide a unitary device which may be positioned in one of several positions for selectively positioning the arm utilizing the single support.

The use of foam in abduction pillows and the like has been done before as is illustrated in U.S. Pat. No. Re. 30,444. A unitary foam block is employed and flat foam strapping is utilized for positioning the wedge shaped abduction pillow for immobilizing the lower limbs as may be necessitated by hip surgery.

SUMMARY OF THE INVENTION

It has been found that a single unitary block of synthetic foam material may be provided in a substantially wedge shape so as to position the arm selectively at approximately 90 degrees to the body or alternatively in a substantially 45 degree relation to the body. In such a block the 90 degree surface and adjacent foam material is used in compression when the 45 degree surface is positioning the arm, whereas when the 90 degree surface is positioning the arm, the 45 degree surface and adjacent foam is utilized in compression to provide firm support for the arm. The 45 degree surface terminates in an outwardly extending portion which serves as an arm rest to support the forearm and at the same time, provides a thickened portion offering adequate support to the forearm without excessive deformation when bearing the weight of the limb. As illustrated in the figures, such arm rest portion acts in conjunction with flanges defined by a free upright support surface to generally apply inward pressure along the upper arm of a patient, and thereby reduce tension on the shoulder joint which has just undergone surgery.

BRIEF DESCRIPTION OF THE DRAWINGS

The construction designed to carry out the invention will be hereinafter described, together with other features thereof.

The invention will be more readily understood from a reading of the following specification and by reference to the accompanying drawings forming a part thereof, wherein an example of the invention is shown and wherein.

DESCRIPTION OF A PREFERRED EMBODIMENT

The drawings illustrate a shoulder abduction splint for supporting the arm of an orthopedic patient constructed from a unitary block of synthetic foam material. A first surface A extends substantially horizontally outwardly from an end portion of an upright support surface C carried against the body of the patient for supporting the upper arm at approximately a 90 degree angle with the body. A second surface B extends outwardly from the other end portion of the upright support surface toward the first surface at an angle for supporting the upper arm at approximately 45 degrees. A free upright surface D opposite the upright support surface is of sufficient depth to afford a thickness of foam to support the forearm and hand of the user adjacent either the first or second surfaces. A foam portion entends along the second surface acting in compression to support the arm when the block is turned so that the first surface supports the arm and acting in tension when said block is turned so that the second surface supports the arm. The block is wedge-shaped having front and rear surfaces diverging outward toward the free upright surface D to provide a support surface for the forearm and hand of the patient. Thus, the arm may be selectively supported in a desired position elected following shoulder surgery. Flat foam straps E are provided for securing said block in position with the upright support surfaces against the body with either first or second support surface uppermost as desired. Such straps are also provided for securing the forearm to the support surface. This second surface B has an arm rest portion extending outwardly therefrom and is illustrated as a concave arcuate portion.

The block may be constructed of polyurethane foam or any foam providing the desirable characteristics of compressibility and flexibility. The surface A is generally flat and is provided with diverging sides 10 and 11 which extend outwardly form the upright surface C. The surface A terminates in an upturned flange 12. The surface A carries transversely spaced Velcro patches 13 and 14 to facilitate the attachment of flat foam strap means for securing the patient's arm to the surface A.

Figure 3:
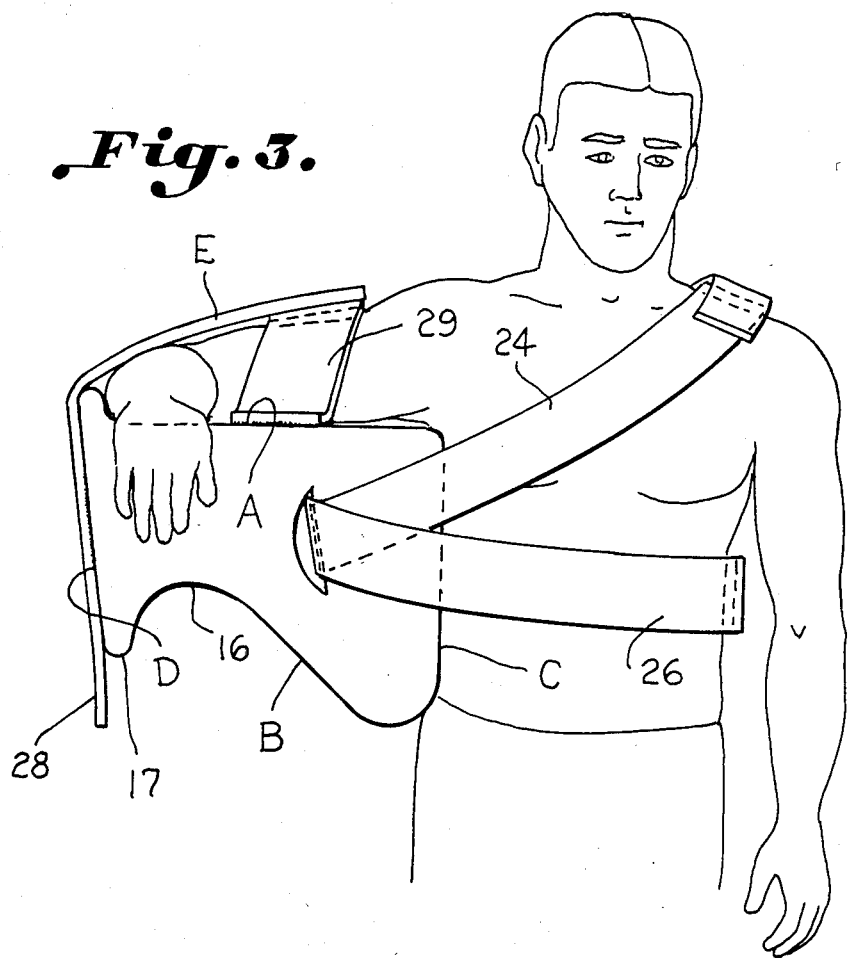
FIG. 3 is a front elevation illustrating the abduction support positioning the arm of the patient at approximately 90 degrees.
Figure 4:
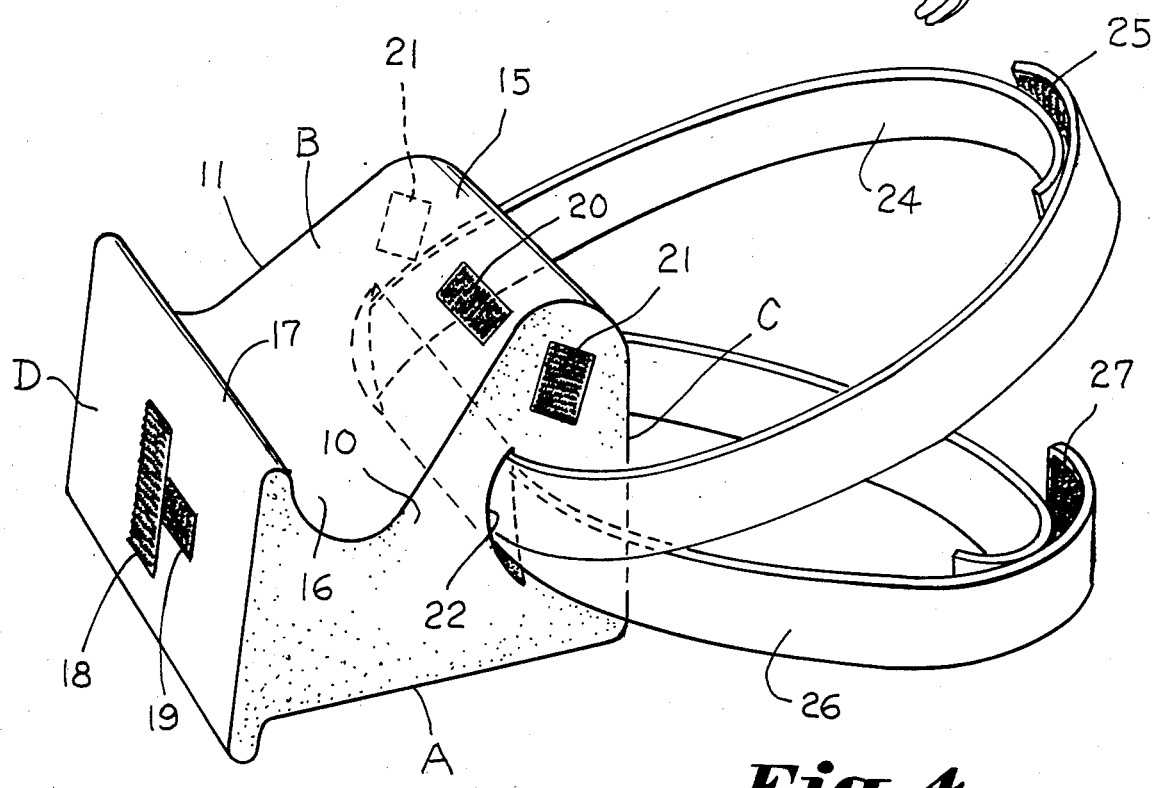
FIG. 4 is an enlarged perspective view illustrating an abduction support constructed in accordance with the present invention with strapping and attachments therefore.
Figure 5:
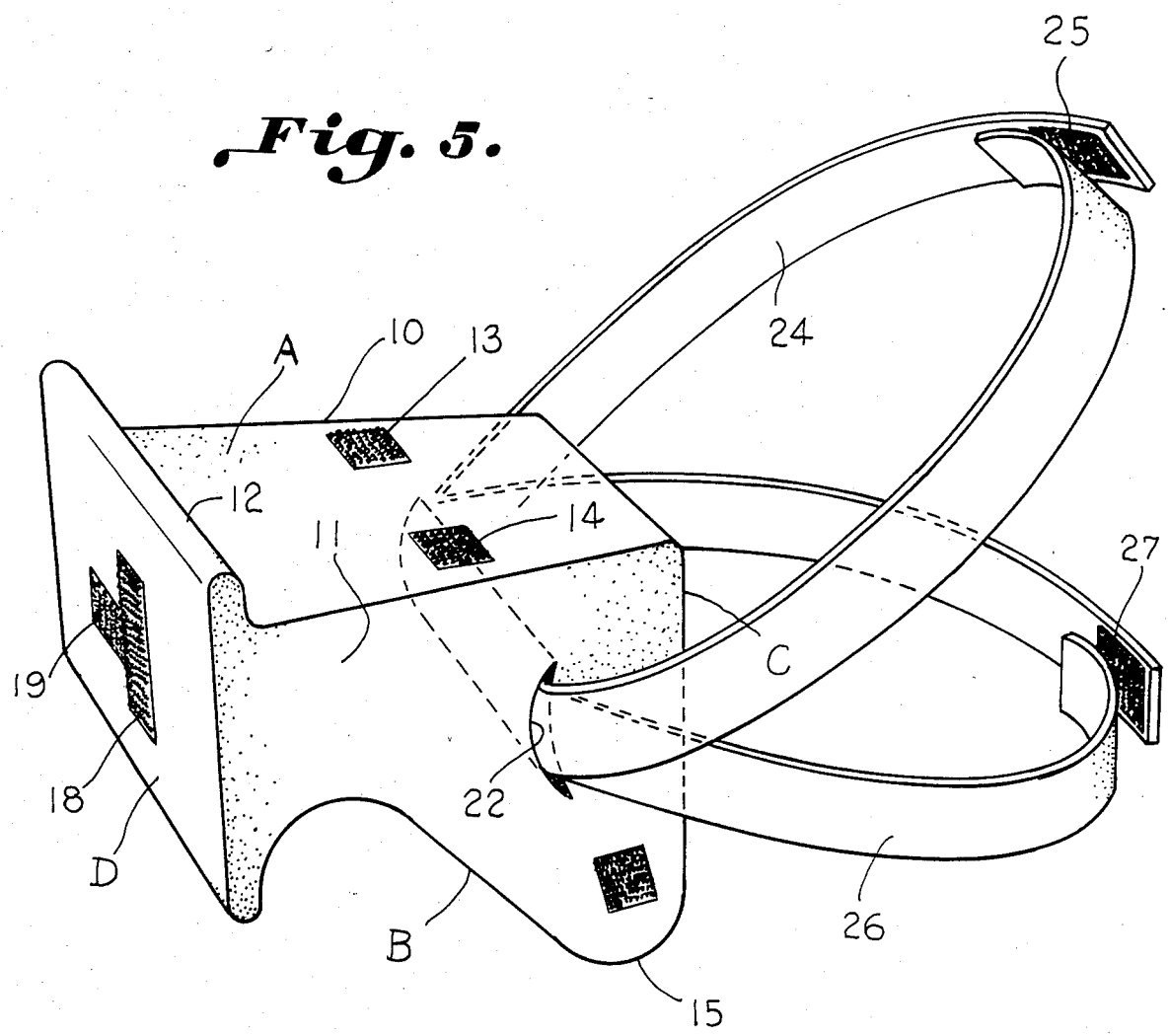
FIG. 5 is a perspective view illustrating the abduction support construction in accordance with the present invention looking toward the free end.
Figure 6:
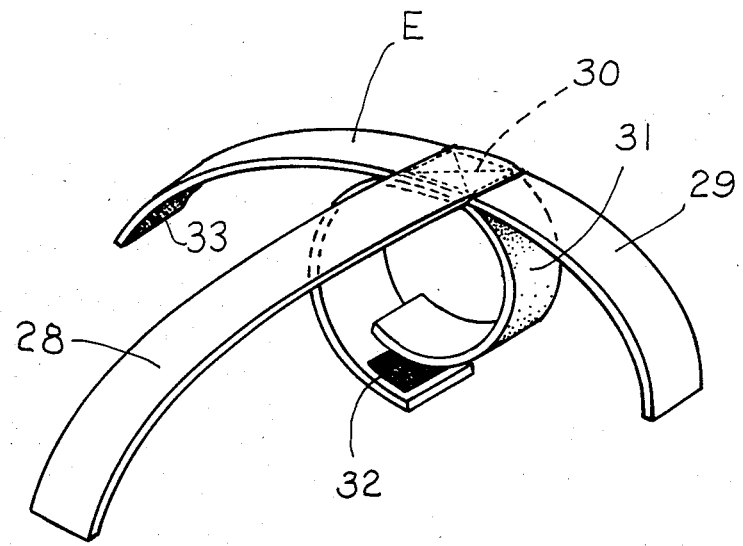
FIG. 6 is a perspective view illustrating strapping for attaching the arm with respect to the abduction pillow.

The surface B is best shown in FIG. 4 and includes an outwardly extending portion tapering downwardly at substantially a 45 degree angle from a curved body portion 15. An outwardly extending arm rest portion 16 extends outwardly from the surface B and extends upwardly to form a flange 17. Upturned flanges 12 and 17 provide a check against outward movement of a patient's elbow to generally apply pressure illustrated respectively in FIGS. 3 and 1 to generally push inwardly at the elbow of the patient along the upper arm to thereby reduce tension on the shoulder joint of the patient.

The flanges 12 and 17 form a portion of the free rear surface D which carries a Velcro strip 18 extending substantially vertically and a horizontal strip 19 to facilitate attachment of the webbing means to position the arm upon the surface B and the arm rest portion 16. The surface B carries a Velcro patch 20 as well as end patches 21 to facilitate attachment of the strapping.

Figure 1:
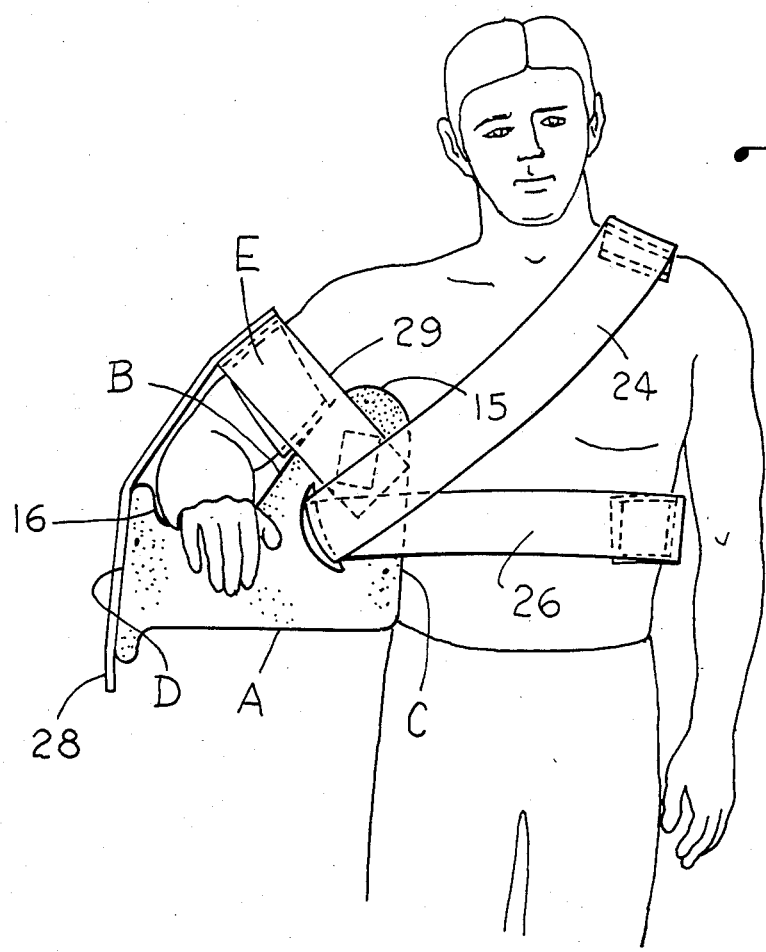
FIG. 1 is a front elevation illustrating an abduction support constructed in accordance with the present invention in position for carrying the arm in a substantially 45 degree position with respect to the body of the patient.
Figure 2:
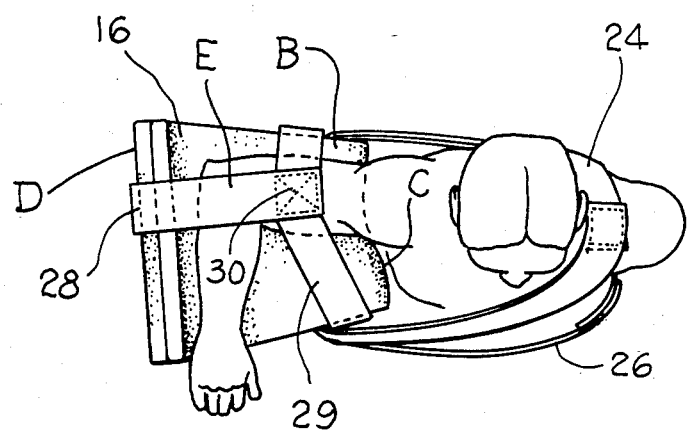
FIG. 2 is a top plan view further illustrating arrangement of FIG. 1.

The block has an opening 22 for positioning a flat strap 24 which is provided with opposed Velcro patches 25 for securing the strap 24 about the shoulders of the patient. Another strap 26 is looped through the opening 22 and is provided with Velcro patches 27 for sewing the strap 26 about the waist of the patient. The strapping means E are provided in the form of flat strips 28 and 29 which are arranged in a substantially T-shaped configuration and sewn together as at 30. Also sewn as at 30 is a loop 31 of foam strapping provided with Velcro fastening members 32 for securing the loop 31 about the upper arm of the wearer as illustrated in FIGS. 1, 2 and 3. The free ends of the members 28 and 29 are provided with Velcro fastening means 33 for securement to the foam block as described above.

Accordingly, it will be observed that a versatile abduction pillow has been provided affording opposite arm rest surfaces such that a unitary block is provided to afford support in one position while the foam adjacent the other surface acts as a structural support for the arm rest portion being used.

While a preferred embodiment of the invention has been described using specific terms, such description is for illustrative purposes only and it is to be understood that changes and variations may be made without departing from the spirit or scope of the following claims.

What is claimed is:

1. A shoulder abduction splint for selectively supporting in one of at least two different orientations the arm of a user, comprising:
    an integral block of resilient material, having
        an upright support surface having two edge portions and adapted to be carried against the body of a user,
        a first surface extending generally perpendicularly from one edge portion of said upright support surface, and adapted for selectively supporting an arm of a user,
        a second surface extending at an angle from another edge portion of said upright support surface towards said first surface, and adapted for selectively supporting an arm of a user,
        a free upright surface, opposite to and parallel with said upright support surface, and having two flange edges, and
        a forearm and hand support surface, opposite to and generally parallel with said first surface, for supporting the forearm and hand of a user whenever said splint is turned such that said second surface is supporting an arm of a user, wherein whenever said splint is turned such that either of said first and second surfaces supports an arm of a user, one of said flanges of said free upright surface applies inward pressure along the length of the upper arm of said user's arm so as to thereby reduce tension on the user's shoulder joint.

2. A splint as in claim 1 wherein said block defines an opening in an intermediate portion of said block opposite said upright support surface adapted for receiving straps therein, and
    further including one strap passing through said opening and adapted to be placed about the waist of a user, and another strap passing through said opening and adapted to be placed over the shoulder of a user for positioning said block adjacent the side of a user in a desired orientation.

3. A splint as in claim 1 wherein said first and second surfaces are generally formed at about a 45 degree angle to each other.

4. A splint as in claim 2 further including a pair of straps associated with said block and adapted to pass over the arm of a user above the elbow thereof, and additional straps having Velcro fastening means for securing said pair of straps to said block.

5. A shoulder abduction splint for supporting the arm of an orthopedic patient, comprising a unitary block of synthetic foam material having:
    a first surface, extending substantially horizontally outwardly from a portion of an upright support surface of said splint adapted to be carried against the body of the patient, for supporting the upper arm at about a 90 degree angle with the patient's body;
    a second surface, extending outwardly at an angle from another portion of said upright support surface toward said first surface, for supporting the upper arm of the patient at about a 45 degree angle with the patient's body;
    a free upright surface, opposite to and parallel with said upright support surface, and
    a foam portion, opposite to and generally parallel with said first surface, extending along said second surface to support the patient's forearm when said block is turned so that said second surface supports the arm; and
    said block being cross-sectionally wedge-shaped and having front and rear surfaces diverging outward toward said free upright surface to define said foam portion and thereby provide a support surface for the forearm and hand of the patient;
    whereby the arm may be selectively supported in a 90 degree or 45 degree position with respect to the patient's body by turning said splint to respectively utilize said first and second surfaces for supporting the arm.

6. The splint as set forth in claim 5 further including flat foam straps for securing said block in position with said upright support surface against the patient's body with either said first or second surface selected to support said arm, and for selectively securing said forearm to said first and second surface.

* * * * *